(12) United States Patent
Takahashi et al.

(10) Patent No.: US 10,842,153 B2
(45) Date of Patent: Nov. 24, 2020

(54) MICROBICIDE AND METHOD FOR MANUFACTURING SAME

(71) Applicants: OPT Creation Inc., Yokohama (JP); SHIGENKAIHATSUKENKYUJYO, INC., Tokyo (JP)

(72) Inventors: Tsunejiro Takahashi, Yokohama (JP); Hideki Yamaguchi, Yokohama (JP); Naoaki Misawa, Miyazaki (JP)

(73) Assignee: OPT CREATION, INC., Yokohama (JP)

( * ) Notice: Subject to any disclaimer, the term of this patent is extended or adjusted under 35 U.S.C. 154(b) by 73 days.

(21) Appl. No.: 15/500,604

(22) PCT Filed: Aug. 3, 2015

(86) PCT No.: PCT/JP2015/071903
§ 371 (c)(1),
(2) Date: Jan. 31, 2017

(87) PCT Pub. No.: WO2016/021523
PCT Pub. Date: Feb. 11, 2016

(65) Prior Publication Data
US 2017/0215428 A1 Aug. 3, 2017

(30) Foreign Application Priority Data
Aug. 4, 2014 (JP) ................ 2014-158862

(51) Int. Cl.
| | | |
|---|---|---|
| *A01N 59/00* | (2006.01) |
| *C01B 13/00* | (2006.01) |
| *C02F 1/78* | (2006.01) |
| *A61K 47/02* | (2006.01) |
| *A61K 9/08* | (2006.01) |
| *B01F 3/04* | (2006.01) |
| *A61K 33/40* | (2006.01) |
| *C02F 1/50* | (2006.01) |
| *B01F 5/04* | (2006.01) |
| *B01F 5/06* | (2006.01) |
| *B01F 5/10* | (2006.01) |
| *C01B 13/10* | (2006.01) |

(52) U.S. Cl.
CPC ............ *A01N 59/00* (2013.01); *A61K 9/08* (2013.01); *A61K 33/40* (2013.01); *A61K 47/02* (2013.01); *B01F 3/04* (2013.01); *B01F 3/0451* (2013.01); *B01F 5/0415* (2013.01); *B01F 5/0688* (2013.01); *B01F 5/0693* (2013.01); *B01F 5/102* (2013.01); *C01B 13/10* (2013.01); *C02F 1/50* (2013.01); *C02F 1/78* (2013.01); *B01F 2003/04886* (2013.01)

(58) Field of Classification Search
None
See application file for complete search history.

(56) References Cited

U.S. PATENT DOCUMENTS

| | | | |
|---|---|---|---|
| 5,951,921 A * | 9/1999 | Koganezawa | ............ C02F 1/78 261/151 |
| 6,207,064 B1 * | 3/2001 | Gargas | ................. B01F 3/0446 210/205 |
| 2007/0205161 A1 | 9/2007 | Chiba et al. | |
| 2010/0186680 A1 | 7/2010 | Matsumura et al. | |

FOREIGN PATENT DOCUMENTS

| | | |
|---|---|---|
| JP | 2005-246293 A | 9/2005 |
| JP | 2006-068631 A | 3/2006 |
| JP | 2007-245075 A | 9/2007 |
| JP | 2009-154076 A | 7/2009 |
| JP | 2009154076 A * | 7/2009 |
| JP | 2012-101222 A | 5/2012 |
| JP | 2012-126649 A | 7/2012 |

OTHER PUBLICATIONS

"Bittern," Written by: The Editors of Encyclopaedia Britannica, <https://www.britannica.com/technology/bittern-chemistry>, published Nov. 17, 2006, p. 1-2.*
EPO Machine English Translation of JP 2009-154076, p. 1-31.*
S. Lillard, "How Ozone Affects Bacteria, Fungus, Molds and Viruses," published Oct. 3, 2004, p. 1-3.*
Communication dated Feb. 1, 2018 from the European Patent Office in counterpart Application No. 15830743.9.
International Search Report of PCT/JP2015/071903 dated Nov. 17, 2015 [PCT/ISA/210].

* cited by examiner

*Primary Examiner* — Monica A Shin
(74) *Attorney, Agent, or Firm* — Sughrue Mion, PLLC

(57) ABSTRACT

Provided is a method for manufacturing a microbicide having high microbicidal performance for eradicating microbes. This method for manufacturing a microbicide comprises: a step for preparing an inorganic aqueous solution containing an inorganic component having seawater as a raw material thereof, an ozone mixing step for mixing ozone into the inorganic aqueous solution, and a stirring step for stirring the inorganic aqueous solution mixed with ozone and passing through a bubble generation nozzle; wherein, the temperature of the inorganic aqueous solution in the ozone mixing step and the stirring step is 0° C. to 30° C., and when the amount of inorganic aqueous solution treated in the ozone mixing step and the stirring step is defined as X liters and the treatment rate of the ozone mixing step and the stirring step is defined as Y liters/minute, then the microbicide is manufactured by alternately repeating the ozone mixing step and the stirring step for A·X/Y minutes (where A is 30 or more).

19 Claims, 2 Drawing Sheets

MICROBICIDE AND METHOD FOR MANUFACTURING SAME

CROSS REFERENCE TO RELATED APPLICATIONS

This application is a National Stage of International Application No. PCT/JP2015/071903, filed Aug. 3, 2015, claiming priority based on Japanese Patent Application No. 2014-158862, filed Aug. 4, 2014, the contents of all of which are incorporated herein by reference in their entirety.

TECHNICAL FIELD

The present invention relates to a method for manufacturing a microbicide for eradicating microbes such as bacteria, fungi and yeast-like fungi, and to a microbicide manufactured according to that manufacturing method.

BACKGROUND ART

Ozone water is used in applications such as microbicides. Ozone water is described in Patent Document 1 as being composed of an aqueous solution containing ozone nanobubbles that have a bubble diameter of 50 nm to 500 nm and contain ozone within the bubbles as an example of ozone water having microbicidal performance.

In addition, Patent Document 2 discloses a prescribed odorless and colorless ozone water comprising a bittern-ozone conjugate, obtained by bonding ozone and a portion of bittern water component, and/or a bittern ozonide, obtained by compounding ozone with a portion of a bittern water component, in a solution containing bittern as an example of ozone water having microbicidal performance.

PRIOR ART DOCUMENTS

Patent Documents

Patent Document 1: JP 2005-246293 A
Patent Document 2: JP 2012-101222 A

DISCLOSURE OF THE INVENTION

Problems to be Solved by the Invention and

Although ozone water can be used in microbicidal applications and the like, when ordinary ozone water manufactured by simply dissolving ozone in water is stored at normal temperatures, a majority of the dissolved ozone is known to end up being depleted in about 1 to 2 weeks after manufacturing. Ozone water containing bittern has been developed as described in Patent Document 2, for example, in order to store ozone having microbicidal performance for a long period of time in an aqueous solution. However, a microbicide is sought that has high microbicidal performance against numerous species of microbes in order to prevent food poisoning and various other diseases.

Therefore, an object of the present invention is to provide a method for manufacturing a microbicide having high microbicidal performance in order to eradicate microbes such as viruses, bacteria, fungi and spores.

Means for Solving the Problems

The present invention employs the following configurations in order to solve the aforementioned problems. The present invention is a method for manufacturing a microbicide characterized by the following Configurations 1 to 12, and a microbicide characterized by the following Configuration 13.

(Configuration 1)

Configuration 1 of the present invention is a method for manufacturing a microbicide, comprising: a step for preparing an inorganic aqueous solution containing an inorganic component having seawater as a raw material thereof, an ozone mixing step for mixing ozone into the inorganic aqueous solution, and a stirring step for stirring the inorganic aqueous solution mixed with ozone and passing through a bubble generation nozzle; wherein, when the amount of inorganic aqueous solution treated in the ozone mixing step and the stirring step is defined as X liters and the treatment rate of the ozone mixing step and the stirring step is defined as Y liters/minute, then the microbicide is manufactured by alternately repeating the ozone mixing step and the stirring step for $A \cdot X/Y$ minutes (where A is 10 or more).

According to the method for manufacturing a microbicide of Configuration 1 of the present invention, a microbicide having high microbicidal performance can be manufactured for eradicating microbes.

(Configuration 2)

Configuration 2 of the present invention is the method for manufacturing a microbicide described in Configuration 1, wherein the temperature of the inorganic aqueous solution in the ozone mixing step and the stirring step is 0° C. to 30° C. A microbicide having higher microbicidal performance can be manufactured by making the temperature of the inorganic aqueous solution in the ozone mixing step and the stirring step to be within a prescribed range in the method for manufacturing a microbicide of the present invention.

(Configuration 3)

Configuration 3 of the present invention is the method for manufacturing a microbicide described in Configuration 1 or Configuration 2, wherein the inorganic component contained in the inorganic aqueous solution contains sodium ions, magnesium ions, potassium ions and calcium ions. A microbicide having high microbicidal performance can be reliably manufactured as a result of the inorganic component contained in the inorganic aqueous solution containing sodium ions, magnesium ions, potassium ions and calcium ions in the method for manufacturing a microbicide of the present invention.

(Configuration 4)

Configuration 4 of the present invention is the method for manufacturing a microbicide described in Configuration 3, wherein the inorganic component contained in the inorganic aqueous solution further contains at least one ion selected from the group consisting of sulfur, boron, lithium, silicon, zinc, iron and strontium ions. A microbicide having high microbicidal performance can be more reliably manufactured as a result of the inorganic component contained in the inorganic aqueous solution further containing the aforementioned ions in the method for manufacturing a microbicide of the present invention.

(Configuration 5)

Configuration 5 of the present invention is the method for manufacturing a microbicide described in any of Configurations 1 to 4, wherein the inorganic aqueous solution is bittern-containing water. An inorganic component for obtaining a microbicide having high microbicidal performance can be provided as a result of the inorganic aqueous solution being bittern-containing water in the method for manufacturing a microbicide of the present invention.

(Configuration 6)

Configuration 6 of the present invention is the method for manufacturing a microbicide described in any of Configurations 1 to 5, wherein the inorganic aqueous solution does not contain organic matter. In the method for manufacturing a microbicide of the present invention, organic matter can be substantially prevented from mixing into the microbicide by making the content of organic matter in the inorganic aqueous solution to be 1 ppm or less. As a result, decreases in microbicidal performance of the microbicide caused by organic matter can be prevented.

(Configuration 7)

Configuration 7 of the present invention is the method for manufacturing a microbicide described in any of Configurations 1 to 6, wherein the bubble generation nozzle is a bubble generation nozzle for generating microbubbles. In the method for manufacturing a microbicide of the present invention, ozone mixed into the inorganic aqueous solution can be made to be in the form of minute bubbles in the manner of microbubbles by using a bubble generation nozzle capable of generating microbubbles. As a result, a microbicide having higher microbicidal performance can be manufactured more reliably.

(Configuration 8)

Configuration 8 of the present invention is the method for manufacturing a microbicide described in any of Configurations 1 to 7, wherein the microbicide is a microbicide for eradicating at least one of viruses, bacteria, fungi and spores. Since a bactericide manufactured according to the manufacturing method of the present invention demonstrates microbicidal performance against prescribed microbes such as viruses, bacteria, fungi and spores, it can be used as a microbicide for eradicating these microbes. In particular, since a microbicide manufactured according to the manufacturing method of the present invention demonstrates microbicidal performance against spores, which were conventionally considered to be difficult to eradicate, it can be used as a microbicide for eradicating spores.

(Configuration 9)

Configuration 9 of the present invention is the method for manufacturing a microbicide described in Configuration 8, wherein the microbicide is a microbicide for eradicating a virus in the form of low pathogenic avian influenza virus (H3N3). Since a microbicide manufactured according to the manufacturing method of the present invention demonstrates microbicidal performance against low pathogenic avian influenza virus (H3N3), it can be used as a microbicide for eradicating low pathogenic avian influenza virus (H3N3).

Configuration 10 of the present invention is the method for manufacturing a microbicide described in Configuration 8, wherein the microbicide is a microbicide for eradicating at least one type of bacteria selected from *Escherichia coli*, *Salmonella enterica*, *Staphylococcus aureus*, *Enterococcus faecalis*, *Campylobacter jejuni*, *Helicobacter cinaedi*, *Helicobacter pylori*, *Vibrio cholerae*, *Vibrio parahaemolyticus*, *Bacillus anthracis* (single seedling strain, two seedling strain), *Treponema* species and *Clostridium botulinum*. Since a microbicide manufactured according to the manufacturing method of the present invention demonstrates microbicidal performance against the aforementioned bacteria, it can be used as a microbicide for eradicating these bacteria.

Configuration 11 of the present invention is the method for manufacturing a microbicide described in Configuration 8, wherein the microbicide is a microbicide for eradicating a fungus in the form of *Aspergillus flavus* or a yeast-like fungus in the form of *Candida albicans*. Since a microbicide manufactured according to the manufacturing method of the present invention demonstrates microbicidal performance against *Aspergillus flavus* or *Candida albicans*, it can be used as a microbicide for eradicating these microbes.

Configuration 12 of the present invention is the method for manufacturing a microbicide described in Configuration 8, wherein the microbicide is a microbicide for eradicating spores of *Bacillus subtilis*. Since a microbicide manufactured according to the manufacturing method of the present invention demonstrates microbicidal performance against spores of *Bacillus subtilis*, which were conventionally considered to be difficult to eradicate, it can be used as a microbicide for eradicating these spores.

Configuration 13 of the present invention is a microbicide manufactured according to the method for manufacturing a microbicide described in any of Configurations 1 to 7. According to the present invention, a microbicide having high microbicidal performance can be obtained for eradicating microbes.

Effects of the Invention

According to the present invention, a method for manufacturing a microbicide having high microbicidal performance can be provided for eradicating microbes such as viruses, bacteria, fungi and spores.

MODE FOR CARRYING OUT THE INVENTION

The present invention is a method for manufacturing a microbicide for eradicating microbes such as viruses, bacteria, fungi and spores. The method for manufacturing a microbicide of the present invention is characterized in that, mixing ozone with an inorganic aqueous solution containing a prescribed inorganic component (ozone mixing step) and carrying out prescribed stirring (stirring step) are repeated for a prescribed amount of time. In addition, the temperature of the inorganic aqueous solution in the ozone mixing step and stirring step is preferably 0° C. to 30° C. Furthermore, a microbicide obtained according to the present invention can be used in the form of a microbicidal aqueous solution.

The prescribed amount of time can be indicated in the form of A·X/Y minutes. Furthermore, X (liters) is the amount of the inorganic aqueous solution treated (treated amount), and Y (liters/min) is the treatment rate of the ozone mixing step and stirring step. The ozone mixing step and stirring step are carried out by alternately circulating the inorganic aqueous solution along the flow paths of the system. Thus, the value of X (liters)/Y (liters/min) corresponds to the time required to carry out one cycle of the ozone mixing step and stirring step. A is a dimensionless quantity corresponding to the number of times treatment is repeated, and A≥10. A microbicide having high microbicidal performance can be manufactured by repeating the ozone mixing step and stirring step for the aforementioned prescribed amount of time.

The following provides a more detailed explanation of the method for manufacturing a microbicide of the present invention.

Figure 1:
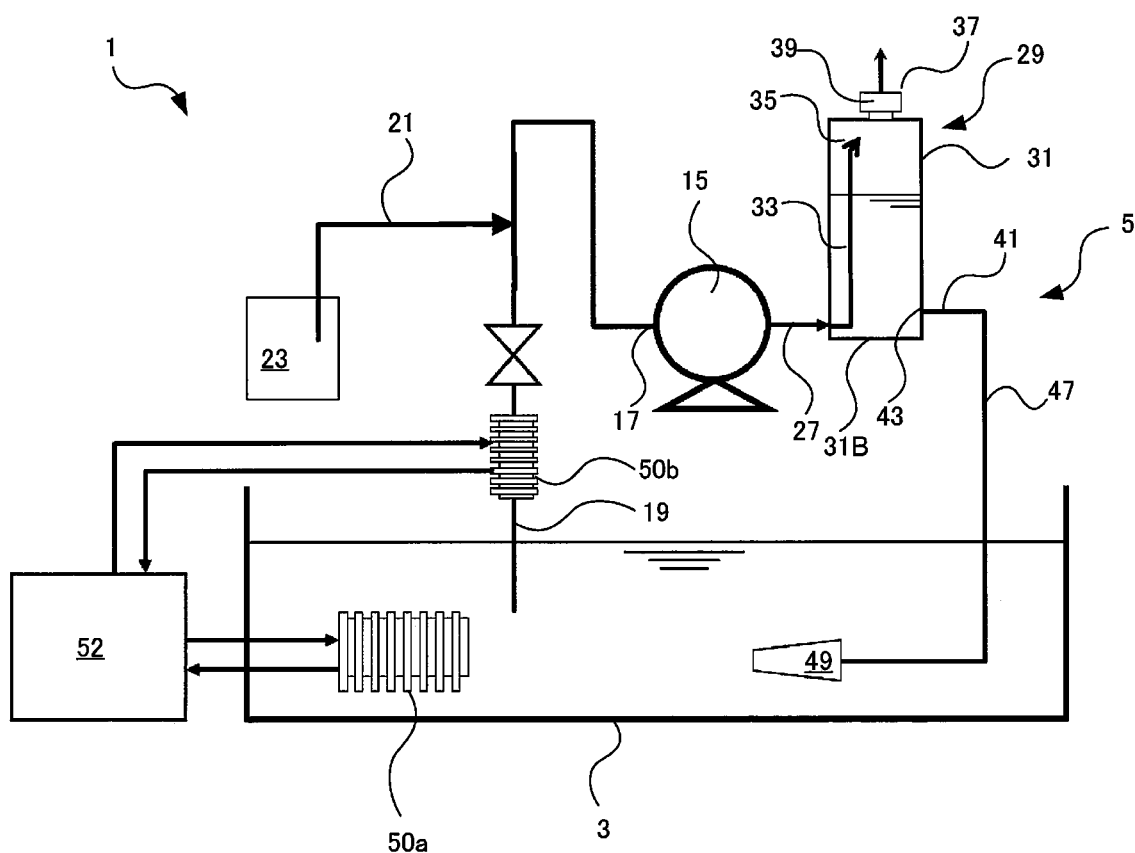
FIG. 1 is a drawing for providing a conceptual and general explanation of a microbicide manufacturing device that can be used in the manufacturing method of the present invention.
Figure 2:
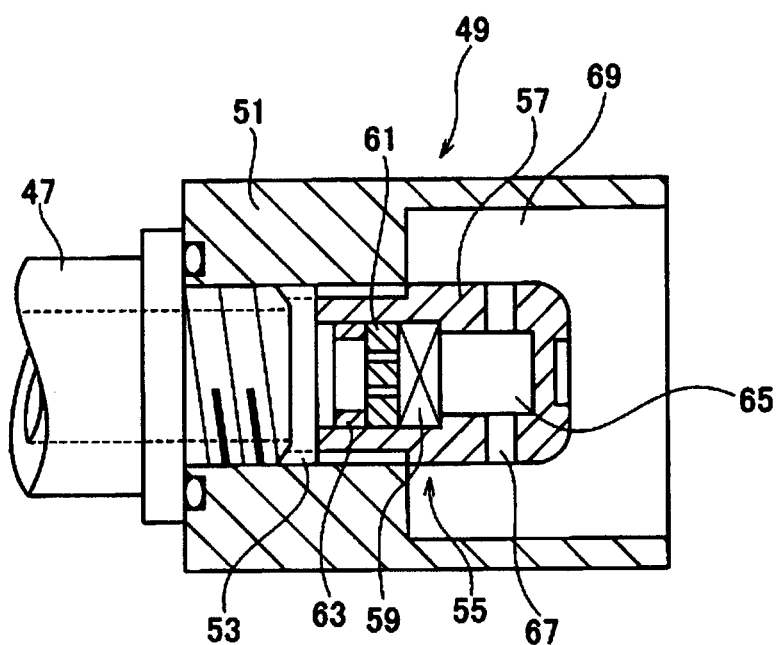
FIG. 2 is a cross-sectional explanatory drawing of a microbubble generation nozzle.

First, an explanation is provided of a device able to be used in the method for manufacturing a microbicide of the present invention using FIGS. 1 and 2. FIG. 1 shows an example of a microbicide manufacturing device 1 that can be used in the method for manufacturing a microbicide of the present invention. The microbicide manufacturing device 1 is provided with a reservoir 3 for storing an inorganic aqueous solution containing a prescribed inorganic component, and a microbubble generation unit 5 for generating microbubbles having a diameter of 1.0 μm to 50 μm in the reservoir 3.

More specifically, the microbubble generation unit 5 can be provided with a casing (not shown). A pump 15 driven to rotate by a motor is installed in the casing. A vortex pump or cascade pump, for example, can be used for the pump 15. The suction port 17 of the pump 15 is connected to the reservoir 3 storing the inorganic aqueous solution via a suction path 19.

A gas suction path 21 for aspirating ozone gas is connected by branching to an intermediate location in the suction path 19 in order to mix ozone into the inorganic aqueous solution aspirated by the pump 15. Since negative pressure is generated in the suction path 19 due to the suctioning action of the pump 15, ozone can be aspirated from the gas suction path 21 into the suction path 19 by connecting the gas suction path 21 to the suction path 19.

An ozone supply means 23 is connected to the gas suction path 21 in order to mix ozone into the inorganic aqueous solution. A configuration in which oxygen supplied from an oxygen tank (not shown) is allowed to pass through an electrical discharge zone can be used for the ozone supply means 23.

The delivery port of the pump 15 is connected to an ozone dissolving unit 29 via a connecting path 27. This ozone dissolving unit 29 is provided with a closed, sealed vessel 31. An inlet pipe 33 connected to the connecting path 27 is provided at a location on the upper side of the sealed vessel 31. The inner end (inlet port) 35 of this inlet pipet 33 is preferably facing the upper side. In addition, the location of the inlet port 35 is slightly above the level of liquid in the sealed vessel 31.

Moreover, a discharge valve 37 is provided in the upper portion of the sealed vessel 31 for discharging excess gas in the form of ozone and oxygen present in the mixing liquid (mixing water) that has been supplied to the sealed vessel 31 by the pump 15. The discharge valve 37 has a function for discharging excess gas from the upper portion of the sealed vessel 31 and a function for maintaining pressure in the sealed vessel 31 at a prescribed pressure higher than atmospheric pressure. A check valve provided with a valve body 39 in the manner of ball, for example, can be used for the discharge valve 37. A small hole is formed for the discharge hole of the check valve used for the discharge valve 37 so as to prevent a large decrease in pressure within the sealed vessel 31.

An outlet pipe 41 is provided near the bottom (bottom surface) 31B of the sealed vessel 31 for allowing the inorganic aqueous solution mixed with ozone in the sealed vessel 31 to flow out to the outside. The inorganic aqueous solution mixed with ozone flows out from an outlet port 43 to the outlet pipe 41.

A bubble generation nozzle 49 is connected to the outlet pipe 41 via a connecting path (connecting pipe) 47. As shown in FIG. 2, this nozzle 49 is provided with a nozzle body 51 connected to the connecting pipe 47. A bubble generation cartridge 55 is removably attached to a communicating hole 53 continuous with the connecting pipe 47 in the nozzle body 51.

More specifically, as show in FIG. 2, the bubble generation cartridge 55 is provided with a cylindrical cartridge body 57 of a form such that one end is closed by a wall portion and the other end is open. A fine-mesh screen member 59 and an orifice 61 provided with a suitable number of small holes are sequentially inserted into the cartridge body 57 through the opening in the other end of the cartridge body 57. Moreover, the screen member 59 and the orifice 61 are removably fixed in position by screwing on a ring-shaped fixture 63 in the manner of a ring-shaped nut or snap ring. A pressure release chamber 65 is provided between the wall portion on one end of the cartridge body 57 and the screen member 59. A plurality of through holes 67 having a diameter smaller than the orifice 61 are formed in the peripheral wall of the pressure release chamber 65.

The one end of the cartridge body 57 protrudes into a stirring chamber 69 composed of a large-diameter hole formed in the nozzle body 51 from the communicating hole 53 in the nozzle body 51. The through holes 67 of the cartridge body 57 are continuous with the stirring chamber 69.

Next, an explanation is provided of an example of the method for manufacturing a microbicide according to the present invention in the case of using the microbicide manufacturing device 1 shown in the aforementioned FIGS. 1 and 2.

To begin with, an inorganic aqueous solution containing an inorganic component having seawater as a raw material thereof is first prepared (step for preparing inorganic aqueous solution). The prepared inorganic aqueous solution is supplied to the reservoir 3. The inorganic aqueous solution will be subsequently described.

Next, ozone is mixed into the inorganic aqueous solution (ozone mixing step). More specifically, when the pump 15 is driven to rotate by operating the motor of the microbicide manufacturing device 1, inorganic aqueous solution in the reservoir 3 is aspirated through the suction path 19 and gas is aspirated through gas suction path 21. This gas contains ozone and oxygen. Consequently, ozone is mixed into the inorganic aqueous solution.

Next, the inorganic aqueous solution mixed with the ozone is stirred in the sealed vessel 31 after which it passes through the bubble generation nozzle 49 (stirring step).

Stirring of the inorganic aqueous solution mixed with ozone can be carried out in the manner indicated below. Namely, inorganic aqueous solution aspirated by the pump 15 of the microbicide manufacturing device 1 and gas containing ozone and oxygen are stirred and mixed in the pump 15, and a portion of the ozone and oxygen is mixed and dissolved in the inorganic aqueous solution. The inorganic aqueous solution in which ozone has been mixed and dissolved is injected into the sealed vessel 31 of the ozone dissolving unit 29 from the inlet port 35 of the inlet pipe 33. Water in the upper portion is stirred by the injected water in the vicinity of the upper portion of the sealed vessel 31, causing a portion of the ozone and oxygen to be dissolved (contained) therein. At this time, excess ozone and oxygen unable to be dissolved (contained) in the water rises to the surface in the sealed vessel 31 and collects at that location, after which they are released to the outside via the discharge valve 37. Namely, a rapid upward flow attributable to the rising of ozone and oxygen in the water in the form of large bubbles occurs in the portion above the inlet port 35.

Furthermore, pressure inside the sealed vessel 31 is constantly maintained at a pressure higher than outside air pressure.

Furthermore, when the inorganic aqueous solution in which the ozone has been mixed and dissolved is injected into the sealed vessel 31 of the ozone dissolving unit 29, the inorganic aqueous solution is injected while directed towards the inner wall by facing the inlet port 35 towards the direction of the inner wall of the sealed vessel 31. As a result of injecting the inorganic aqueous solution towards the inner wall, mixing and dissolving of ozone in the inorganic aqueous solution can be carried out more efficiently.

After stirring the inorganic aqueous solution in which the ozone is dissolved, the inorganic aqueous solution is passed through the bubble generation nozzle 49. More specifically, the inorganic aqueous solution in which the ozone is mixed and dissolved in the vicinity of the bottom 31B of the sealed vessel 31 is supplied to the bubble generation nozzle 49 from the outlet pipe 41 of the microbicide manufacturing device 1 through the connecting pipe 47.

When the inorganic aqueous solution containing ozone that has flown in from the connecting pipe 47 to the nozzle 49 passes through the small holes in the orifice 61, the release of pressure causes the ozone and oxygen dissolved (contained) in the ozone-containing inorganic aqueous solution to be generated in the form of fine bubbles. These generated fine bubbles are injected into the pressure release chamber 65 after having been further reduced in size by the screen member 59. Since the pressure of the ozone-containing inorganic aqueous solution is further released in the pressure release chamber 65, in addition to gas being further generated in the form of fine bubbles, the fine bubbles collide with the wall portion on one end of the pressure release chamber 65, thereby making them even finer.

After having been injected from the pressure release chamber 65 into the stirring chamber 69 by passing through the through holes 67, the ozone-containing inorganic aqueous solution generates even finer bubbles as a result of being subjected to further release of pressure. In addition thereto, bubbles in the inorganic aqueous solution are made even finer by stirring action, thereby resulting in the generation of uniform microbubbles having a diameter of about 1 μm to 50 μm.

The inorganic aqueous solution initially becomes milky white when the aforementioned microbubbles are generated in water. A colorless and odorless microbicide is formed as the solution becomes transparent as a result of the microbubbles collapsing by pressure over time.

As is already understood, an odorless and colorless microbicide is formed (manufactured) in the reservoir 3 as a result of generating ozone microbubbles having a diameter of 1.0 μm to 50 μm in an inorganic aqueous solution containing ozone that has been suitably dissolved (contained) in the inorganic aqueous solution.

In the method for manufacturing a microbicide of the present invention, when the amount of inorganic aqueous solution treated in the aforementioned ozone mixing step and the stirring step is defined as X liters and the treatment rate of the ozone mixing step and the stirring step is defined as Y liters/minute, then the microbicide is manufactured by alternately repeating the ozone mixing step and the stirring step for A·X/Y minutes (where A is 10 or more). The inventors of the present invention found that, by making the time during which a prescribed inorganic aqueous solution mixed with ozone is treated to be the aforementioned prescribed amount of time, a microbicide having high microbicidal performance can be manufactured for eradicating microbes such as viruses, bacteria, fungi and spores, thereby leading to completion of the present invention.

Furthermore, the ozone mixing step and stirring step are preferably alternately repeated continuously. A microbicide having high microbicidal performance can be manufactured by alternately repeating these steps continuously. Alternatively, the ozone mixing step and stirring step can also be alternately repeated intermittently.

In the example of the microbicide manufacturing device 1 shown in FIG. 1, the amount of inorganic aqueous solution prepared in the step for preparing an inorganic aqueous solution and supplied to the reservoir 3 (treated amount) corresponds to the value of X liters. When manufacturing a microbicide by operating the microbicide manufacturing device 1, the treated amount of X liters of the inorganic aqueous solution is present in reservoir 3, inside the pump 15 and in the sealed vessel 31 of the microbicide manufacturing device 1, and in piping such as the inlet pipe 33 or outlet pipe 41 that connects them, in a state in which ozone is mixed and stirred therein.

In the example of the microbicide manufacturing device 1 shown in FIG. 1, the ozone mixing step and stirring step are carried out by alternately circulating the inorganic aqueous solution along the flow paths of the system. Thus, the treatment rate (Y liters/min) of the ozone mixing step and stirring step is determined by the flow rate of the pump 15. The treatment rate (Y liters/min) can therefore be controlled by controlling the flow rate of the pump 15. X (liters)/Y (liters/min) corresponds to the time required to carry out one cycle of the ozone mixing step and stirring step.

The aforementioned A is a dimensionless quantity corresponding to the number of times treatment is repeated. A is 10 or more, preferably 20 or more, preferably within the range of 20 to 150, more preferably within the range of 30 to 150, even more preferably within the range of 40 to 80, and particularly preferably within the range of 45 to 60. As a result of carrying out the ozone mixing step and stirring step for the aforementioned prescribed amount of time by circulating the inorganic aqueous solution through the microbicide manufacturing device 1 with the pump 15, the ozone mixing step and stirring step can be carried out repeatedly. As a result, a microbicide having high microbicidal performance can be manufactured.

In the method for manufacturing a microbicide of the present invention, the temperature of the inorganic aqueous solution in the ozone mixing step and stirring step is preferably 0° C. to 30° C., can be 0° C. to 25° C., can be 0° C. to 15° C., is more preferably 0° C. to 10° C., is even more preferably 2° C. to 9° C. and is particularly preferably 3° C. to 6° C. A microbicide having higher microbicidal performance can be manufactured by making the temperature of the inorganic aqueous solution in the ozone mixing step and stirring step to be within a prescribed range in the method for manufacturing a microbicide of the present invention.

A temperature control mechanism can be provided for controlling the temperature of the inorganic aqueous solution circulating through the microbicide manufacturing device 1 in order to make the temperature of the inorganic aqueous solution to be within the prescribed range. As shown in FIG. 1, an example of a temperature control mechanism consists of making it possible to control the temperature of the inorganic aqueous solution in the reservoir 3 by circulating a heat exchange medium such as a coolant at a prescribed temperature between a temperature control mechanism body 52 and a heat exchanger 50a arranged in the reservoir 3. The heat exchange medium in the temperature control mechanism body 52 can be controlled to a prescribed temperature by using a feedback loop based on the value of the temperature of the inorganic aqueous solution as measured by a temperature sensor (not shown) arranged in the reservoir 3. The temperature control mechanism is preferably arranged in the reservoir 3 as shown in FIG. 1. This is because a large volume of the inorganic aqueous solution circulating through the microbicide manufacturing device 1 is present in the reservoir 3. Furthermore, the heat exchanger 50a can be arranged at arbitrary locations in the path by which the inorganic aqueous solution circulates through the microbicide manufacturing device 1 other than the reservoir 3, examples of which include the pump 15, sealed vessel 31 and piping that connects them. In the example of FIG. 1, a heat exchanger 50b is also arranged in the suction path 19 in addition to the reservoir 3. A temperature control mechanism for controlling the temperature of an aqueous solution in the manner of the inorganic aqueous solution is known.

In the method for manufacturing a microbicide of the present invention, the bubble generation nozzle 49 is preferably a bubble generation nozzle 49 for generating microbubbles. More specifically, as a result of using the bubble generation nozzle 49 as shown in FIG. 2 in the stirring step, ozone mixed into the inorganic aqueous solution can become the form of fine bubbles in the manner of microbubbles. As a result, a microbicide having higher microbicidal performance can be manufactured more reliably.

Next, an explanation is provided of the inorganic aqueous solution able to be used in the method for manufacturing a microbicide of the present invention. The inorganic aqueous solution contains an inorganic component having seawater as a raw material thereof. As a result of subjecting the inorganic aqueous solution to a prescribed treatment, the inorganic component having seawater as a raw material thereof and ozone are transformed into a compound having high microbicidal performance, and this is presumed to allow the obtaining of a microbicide.

In the method for manufacturing a microbicide of the present invention, the inorganic component contained in the inorganic aqueous solution preferably contains at least one ion selected from sodium ions, magnesium ions, potassium ions and calcium ions, and preferably contains all of the aforementioned ions. In addition, the inorganic component contained in the inorganic aqueous solution preferably further contains at least one ion selected from the group consisting of sulfur, boron, lithium, silicon, zinc, iron and strontium ions. As a result, a microbicide having high microbicidal performance can be reliably manufactured.

In the method for manufacturing a microbicide of the present invention, the inorganic aqueous solution preferably contains bittern-containing water.

"Bittern" is a liquid that remains after precipitating salt from seawater. Bittern contains at least one type of ion selected from the group consisting of sodium ions, magnesium ions, potassium ions and calcium ions, and depending on the case, sulfur, boron, lithium, silicon, zinc, iron and strontium ions. Consequently, water containing bittern can be preferably used for the inorganic aqueous solution used in the method for manufacturing a microbicide of the present invention.

Examples of bittern-containing water that can be used include "Amami-no-Nigari (a trade name)" (Amami Bittern) and "Shinsousui Nigari Gyomuyo" (Deep Seawater Bittern for professional use) (both available from Ako Kasei Co., Ltd.). In addition, deep sea water contains little organic matter. Since microbicidal performance tends to decrease in the case the microbicide of the present invention contains organic matter, bittern-containing water with deep sea water as a raw material thereof is preferably used for the inorganic aqueous solution used in the method for manufacturing a microbicide of the present invention.

The inorganic aqueous solution used in the method for manufacturing a microbicide of the present invention preferably does not contain organic matter. The microbicidal performance of microbicides tends to decrease if organic matter is present therein. Consequently, a microbicide can be made to be substantially free of organic matter by making the content of organic matter in the inorganic aqueous solution to be as low as possible (for example, 1 ppm or less). As a result, decreases in microbicidal performance of the microbicide attributable to the presence of organic matter can be prevented.

A microbicide manufactured according to the method for manufacturing a microbicide of the present invention (to simply be referred so as the "microbicide of the present invention") has a high level of microbicidal performance. Consequently, the microbicide of the present invention can be used as a microbicide for eradicating at least one type of microbe, such as viruses, bacteria, fungus or spores.

The microbicide of the present invention has been confirmed to be able to be used as a microbicide for eradicating viruses such as low pathogenic avian influenza virus (H3N3). In addition, the microbicide of the present invention has been confirmed to be able to be used as a microbicide for eradicating bacteria such as *Escherichia coli*, *Salmonella enterica*, *Staphylococcus aureus*, *Enterococcus faecalis*, *Campylobacter jejuni*, *Helicobacter cinaedi*, *Helicobacter pylori*, *Vibrio cholerae*, *Vibrio parahaemolyticus*, *Bacillus anthracis* (single seedling strain, two seedling strain), *Treponema* species and *Clostridium botulinum* (botulinum toxin type A and botulinum toxin type B). In addition, the microbicide of the present invention has been confirmed to be able to be used as a microbicide for eradicating fungi such as *Aspergillus flavus*. In addition, the microbicide of the present invention has been confirmed to be able to be used as a microbicide for eradicating yeast-like fungi such as *Candida albicans*. In addition, the microbicide of the present invention has been confirmed to be able to be used as a microbicide for eradicating spores of *Bacillus subtilis*, botulinum toxin type A (spores) and botulinum toxin type B (spores). In addition, the microbicide of the present invention is considered to be effective as an anthrax microbicide since it is effective as a microbicide against the aforementioned bacteria. Thus, a microbicide manufactured according to the manufacturing method of the present invention can be used as a microbicide against the aforementioned viruses, bacteria, fungi and spores.

The microbicide of the present invention is not limited to the aforementioned embodiments, but rather can be carried out in other forms by making suitable modifications thereto. Namely, a solution obtained by adding an inorganic component, which has been adjusted to mimic the components of sea water, to an aqueous solution not containing impurities such as soft water, can be used instead of seawater for the inorganic aqueous solution.

EXAMPLES

Experimental Example 1

The microbicides of Experimental Example 1 were manufactured using the microbicide manufacturing device 1 shown in FIG. 1 by setting so as to maintain the temperature of the treated inorganic aqueous solution to 4° C. and varying the treatment time as shown in Table 1. At that time, the bubble generation nozzle 49 for generating microbubbles shown in FIG. 2 was used for the bubble generation nozzle 49. As shown in Table 1, the amount of inorganic aqueous solution supplied to the reservoir 3 of the microbicide manufacturing device 1 (treated amount X) is 12 liters. In addition, the treatment rate Y of the microbicide manufacturing device 1 is 10 liters/min. As shown in Table 1, microbicides were manufactured while varying the treatment time t from 15 minutes to 150 minutes. At this time, the values of A (=t·Y/X) corresponding to the number of times treatment was repeated are the values shown in Table 1. In the microbicide manufacturing device 1 shown in FIG. 1, the ozone mixing step and stirring step were alternately repeated continuously.

Bittern-containing water ("Shinsousui Nigari Gyomuyo" (Deep Seawater Bittern for professional use, Ako Kasei Co., Ltd.) was used for the inorganic aqueous solution used in Experimental Example 1 after diluting three-fold with water (tap water). "Shinsousui Nigari Gyomuyo" contains 12% to 30% by weight $MgCl_2$ as Mg ions as well as 10 mg/liter to 100 mg/liter of Ca ions, 100 mg/liter to 1000 mg/liter of K ions and 100 mg/liter to 1000 mg/liter of Na ions.

The ozone concentrations of the manufactured microbicides were measured with an ozone concentration sensor and according to the KI method. Microbicidal performance of the manufactured microbicides was evaluated according to the "Maximum dilution factor having a microbicidal effect" to be subsequently described. Furthermore, these measurements and evaluations were carried out 24 hours after manufacturing the microbicides of Experimental Example 1. During that time, the microbicides of Experimental Example 1 were placed in a covered container and stored in a refrigerator at 4° C. while covered.

The Model OZ-20 Ozone Meter manufactured by DKK-Toa Corp. was used for the ozone concentration sensor.

Measurement according to the KI method was carried out in the manner indicated below. Namely, the KI method is a measurement method that uses the release of $I_2$ from KI in the presence of an oxidant. Here, the reaction between ozone ($O_3$), iodine ($I_2$) and sodium thiosulfate ($Na_2S_2O_3$) takes place at a molar ratio of 1:1:2. The molecular weight of $O_3$ is 16.00×3=48, the molecular weight of $I_2$ is 126.9×2=253.8, and the molecular weight of $Na_2S_2O_3$ is 22.9+32.07×2+16× 3≈158.

Since the reaction between ozone and sodium thiosulfate takes place at a molar ratio of 1:2, the weight ratio of ozone to sodium thiosulfate is 48:(2×158), and when the amount of ozone present in 1 liter of microbicide is defined as X (g), and the number of ml of 1/100 normal (N) $Na_2S_2O_3$ (sodium thiosulfate) is defined as B, then:

$$(48/2)/158 = X/(B/1000) \times (158/100), \text{ and}$$

$$X = 0.24B \times 10^{-3} \text{ (g)} = 0.24B \text{ mg (ppm)}.$$

In measuring ozone concentration as described above, a starch solution is first prepared by dissolving starch in 50 to 100 ml of water (distilled water). In addition, a hydrochloric acid solution is prepared by diluting hydrochloric acid (HCl) having a concentration of 35% five-fold with water. A KI solution is prepared by dissolving 20 g of potassium iodide (KI) in 100 ml of water. A 1/100 N $Na_2S_2O_3$ solution is prepared by dissolving $Na_2S_2O_3$ in water. Next, 1 liter of microbicide is placed in a 2-liter glass beaker, and when 20 ml of the starch solution, 20 ml of the KI solution and 10 ml of the hydrochloric acid solution are placed in the beaker and mixed well, the resulting solution takes on a light purple color.

The resulting solution is then titrated with the 1/100 N $Na_2S_2O_3$ solution, and the titrated amount is read when the light purple color disappears and the solution becomes clear and colorless. Here, in the case of titrating with 1 ml, the ozone concentration is 0.24×1=0.24 ppm, while in the case of titrating with 5 ml, the ozone concentration is 0.24×5=1.2 ppm. Namely, ozone concentration can be measured (estimated) according to the KI method based on the titrated amount of 1/100 N $Na_2S_2O_3$ solution.

In the case of ordinary ozone water, once the light purple color has disappeared and the resulting solution becomes colorless and clear when measuring ozone concentration according to the KI method, the solution does not again become light purple. However, in the case of the microbicides of Experimental Example 1, after having titrated with the 1/100 N $Na_2S_2O_3$ solution and the resulting solution becomes colorless and clear, the solution again changes to a light purple color after several minutes to several tens of minutes. Thus, in the case of repeating titration with the 1/100 N $Na_2S_2O_3$ solution until the resulting solution becomes colorless and clear several times, and the resulting solution has not changed to a light purple color after a prescribed amount of time, such as after 60 minutes have passed, ozone concentration is measured (estimated) based on the entire amount of the titrated 1/100 N $Na_2S_2O_3$ solution. Furthermore, it is preferable to make the prescribed amount of time as long as possible in order to measure ozone concentration with higher accuracy.

The results for measuring ozone concentration in Experimental Example 1 are shown in Table 1. According to measurement of ozone concentration with an ozone concentration sensor, measured values were zero for all microbicides evaluated in Experimental Example 1. On the other hand, values measured according to the KI method increased monotonically from 82.1 ppm (treatment time t=15 minutes) to 310.6 ppm (treatment time t=150 minutes) as treatment time increased as shown in Table 1.

In order to evaluate microbicidal performance of the microbicides of Experimental Example 1 manufactured by varying treatment time as shown in Table 1, the microbicides of Experimental Example 1 were diluted at a prescribed dilution factor and applied to the ATCC type strain (ATCC accession no. 25922) of *Escherichia coli* followed by measurement of the number of *E. coli* that survived. A value of ">300" recorded for the "Microbial count after eradication" indicates that the number of *Escherichia coli* exceeded the measuring limit of the measuring instrument, and means that the microbicide did not demonstrate a microbicidal effect. On the other hand, in the case the "Microbial count after eradication" in Table 1 is 300 or less, this means that the microbicide demonstrated a microbicidal effect. The maximum dilution factor at which the microbicide demonstrated a microbicidal effect is indicated in the column of Table 1 entitled "Maximum dilution factor having a microbicidal effect". A larger value for the "Maximum dilution factor having a microbicidal effect" can be said to indicate that the microbicide demonstrates high microbicidal performance.

Microbicidal performance of the microbicides of Experimental Example 1 is indicated as the number of microbes surviving following eradication by a prescribed microbicide. As shown in Table 1, in the case A is 10 or more, the maximum dilution factor having a microbicidal effect is 800-fold or more, and the microbicide can be said to have microbicidal performance for use as a microbicide. In addition, as shown in Table 1, in the case A is 25 or more, the maximum dilution factor having a microbicidal effect is 1000-fold or more, and such a microbicide can be said to have more favorable microbicidal performance for use as a microbicide. In addition, in Experimental Example 1, microbicides were confirmed to demonstrate microbicidal performance for use as a microbicide in the case A is within a range of 10 to 150, preferably within a range of 20 to 150 and more preferably within a range of 30 to 150. In addition, in the case A is 50, the maximum dilution factor having a microbicidal effect was confirmed to be 4000-fold, demonstrating an extremely high level of microbicidal performance. Consequently, a microbicide having an extremely high level of microbicidal performance can be said to be able to be manufactured by making A to be 40 or more, preferably within the range of 40 to 80 and more preferably within the range of 45 to 60.

Furthermore, measured values for ozone concentration according to the KI method increased monotonically relative to the increase in A. However, as was previously described, in the case A is in the vicinity of 50, the maximum dilution factor having a microbicidal effect becomes 4000-fold, and microbicidal performance of the microbicide of the present invention can be said to demonstrate peak microbicidal performance. Thus, even if the microbicides of Experimental Example 1 contain a detectable level of ozone according to the KI method, it is presumed that ozone alone cannot be said to demonstrate a microbicidal effect. Thus, a microbicide manufactured according to the manufacturing method of the present invention is presumed to not consist of ozone water alone, but rather be the result of some form of chemical bonding between ozone and the inorganic component having seawater as a raw material thereof, and microbicidal performance is demonstrated as a result thereof. However, the present invention is not bound by the present presumption.

Experimental Example 2

The microbicides of Experimental Example 2 were manufactured in the same manner as Experimental Example 1 with the exception of setting the set aqueous solution temperature of the treated inorganic aqueous solution to 10° C. Subsequently, the ozone concentrations of the microbicides of Experimental Example 2 were measured with an ozone concentration sensor and according to the KI method in the same manner as Experimental Example 1. In addition, the "Maximum dilution factor having a microbicidal effect" was measured for the microbicides of Experimental Example 2. The results are shown in Table 2.

As shown in Table 2, in the case A is 10 or more, the maximum dilution factor having a microbicidal effect was 800-fold or more, and the microbicides can be said to have microbicidal performance for use as a microbicide. In addition, as shown in Table 2, in the case A is 25 or more, the maximum dilution factor having a microbicidal effect was 1000-fold or more, and the microbicides can be said to have more favorable microbicidal performance for use as a microbicide. In addition, in Experimental Example 2, the microbicides were confirmed to have microbicidal performance for use as a microbicide in the case A is within the range of 10 to 150, preferably within the range of 20 to 150 and more preferably within the range of 30 to 150.

As was previously described, in the case A is in the vicinity of 50, the maximum dilution factor having a microbicidal effect becomes 4000-fold, and microbicidal performance of the microbicides of Experimental Example 2 clearly demonstrates peak microbicidal performance in the same manner Experimental Example 1. Consequently, a microbicide demonstrating an extremely high level of microbicidal performance can be said to be able to be manufactured by making A to be 40 or more, preferably within the range of 40 to 80 and more preferably within the range of 45 to 60.

Experimental Example 3

The microbicides of Experimental Example 3 were manufactured in the same manner as Experimental Example 1 with the exception of setting the set aqueous solution temperature of the treated inorganic aqueous solution to 25° C. Subsequently, the ozone concentrations of the microbicides of Experimental Example 3 were measured with an ozone concentration sensor and according to the KI method in the same manner as Experimental Example 1. In addition, the "Maximum dilution factor having a microbicidal effect" was measured for the microbicides of Experimental Example 3. The results are shown in Table 3.

The maximum dilution factor having a microbicidal effect of the microbicides of Experimental Example 3 was about 1000-fold, and although this is lower than that of the microbicides of Experimental Example 1 and Experimental Example 2, microbicidal effects for use as a microbicide were demonstrated.

Experimental Example 4

The microbicides of Experimental Example 4 were manufactured in the same manner as Experimental Example 1 with the exception of setting the set aqueous solution temperature of the treated inorganic aqueous solution to 50° C. Subsequently, the ozone concentrations of the microbicides of Experimental Example 4 were measured with an ozone concentration sensor and according to the KI method in the same manner as Experimental Example 1. In addition, the "Maximum dilution factor having a microbicidal effect" was measured for the microbicides of Experimental Example 4. The results are shown in Table 4.

The maximum dilution factor having a microbicidal effect of the microbicides of Experimental Example 4 was about 500-fold, and although this was lower than that of the microbicides of Experimental Examples 1 to 3, microbicidal effects for use as a microbicide can be said to have been demonstrated. Thus, microbicidal effects for use as a microbicide can be said to demonstrated in the A is 10 or more.

On the basis of the results the previously described Experimental Examples 1 to 4, microbicides having high microbicidal performance, for which A is 10 or more and preferably 30 or more, were clearly able to be manufactured at a temperature of the inorganic aqueous solution in the ozone mixing step and stirring step of 4° C. (Experimental Example 1) and 10° C. (Experimental Example 2). In addition, in the case A is within the range of 40 to 80, preferably 45 to 60, and specifically about 50, microbicides were clearly able to be manufactured that have an extremely high level of microbicidal performance.

Furthermore, in contrast to the ozone being unstable and said to decrease by half in just over ten minutes in the case of typically producing a microbicide by blowing ozone gas into water, in the case of a microbicide manufactured according to the manufacturing method of the present invention, microbicidal performance was confirmed to be maintained at a nearly constant level even after three months.

Experimental Example 5

The microbicide of Experimental Example 5 was manufacturing using the same microbicide as the microbicide of Experimental Example 2 in which treatment time was 50 minutes (A=50). Microbicidal efficacy against microbes such as the various types of bacteria shown in Table 5 was evaluated using the microbicide of Experimental Example 5. Evaluation of the microbicide of Experimental Example 5 was carried out by measuring the "Maximum dilution factor having a microbicidal effect" as previously described. The results are shown in Table 5. As is clear from Table 5, the microbicide of the present invention was confirmed to be effective as a microbicide against all of the bacteria indicated in Table 5. In addition, it was also separately confirmed to be effective as a microbicide against low pathogenic avian influenza virus (H3N3).

TABLE 1

| Treatment time t (min) | | 0 | 15 | 30 | 45 | 60 | 90 | 120 | 150 |
|---|---|---|---|---|---|---|---|---|---|
| Treated amount X (liters) | | — | 12 | 12 | 12 | 12 | 12 | 12 | 12 |
| Treatment rate Y (liters/min) | | — | 10 | 10 | 10 | 10 | 10 | 10 | 10 |
| A(=t · Y/X) | | — | 12.5 | 25 | 37.5 | 50 | 75 | 100 | 125 |
| Set aqueous solution temperature (° C.) | | 4 | 4 | 4 | 4 | 4 | 4 | 4 | 4 |
| Measurement according to KI method (ppm) | | 0 | 82.1 | 135.4 | 190.1 | 216.5 | 246.7 | 283.2 | 310.6 |
| Ozone concentration measured with ozone concentration sensor (ppm) | | 0 | 0 | 0 | 0 | 0 | 0 | 0 | 0 |
| Microbial count after eradication | Microbicide dilution factor ↓ | — | — | — | — | — | — | — | — |
| | 400-fold | — | 0 | 0 | — | 0 | — | 0 | 0 |
| | 800-fold | — | 0 | 0 | — | 0 | — | 0 | 0 |
| | 1000-fold | — | >300 | 0 | — | 0 | — | 0 | 0 |
| | 2000-fold | — | >300 | >300 | — | 0 | — | 0 | 0 |
| | 4000-fold | — | >300 | >300 | — | 128 | — | >300 | >300 |
| | 8000-fold | — | >300 | >300 | — | >300 | — | >300 | >300 |
| Maximum dilution factor having a microbicidal effect | | — | 800-fold | 1000-fold | — | 4000-fold | — | 2000-fold | 2000-fold |

TABLE 2

| Treatment time t (min) | 0 | 15 | 30 | 60 | 120 | 150 |
|---|---|---|---|---|---|---|
| Treated amount X (liters) | — | 12 | 12 | 12 | 12 | 12 |
| Treatment rate Y (liters/min) | — | 10 | 10 | 10 | 10 | 10 |
| A(=t · Y/X) | — | 12.5 | 25 | 50 | 100 | 125 |
| Set aqueous solution temperature (° C.) | 10 | 10 | 10 | 10 | 10 | 10 |
| Measurement according to KI method (ppm) | 0 | 81.6 | 146.9 | 205.4 | 270.2 | 297.6 |
| Maximum dilution factor having a microbicidal effect | — | 800-fold | 2000-fold | 4000-fold | 2000-fold | 2000-fold |

TABLE 3

| Treatment time t (min) | 0 | 15 | 30 | 60 | 120 | 150 |
|---|---|---|---|---|---|---|
| Treated amount X (liters) | — | 12 | 12 | 12 | 12 | 12 |
| Treatment rate Y (liters/min) | — | 10 | 10 | 10 | 10 | 10 |
| A(=t · Y/X) | — | 12.5 | 25 | 50 | 100 | 125 |
| Set aqueous solution temperature (° C.) | 25 | 25 | 25 | 25 | 25 | 25 |
| Measurement according to KI method (ppm) | 0 | 78.7 | 131.0 | 203.5 | 300.0 | 305.3 |
| Maximum dilution factor having a microbicidal effect | — | 1000-fold | 1000-fold | 1000-fold | 2000-fold | 1000-fold |

TABLE 4

| Treatment time t (min) | 0 | 15 | 30 | 60 | 120 | 150 |
|---|---|---|---|---|---|---|
| Treated amount X (liters) | — | 12 | 12 | 12 | 12 | 12 |
| Treatment rate Y (liters/min) | — | 10 | 10 | 10 | 10 | 10 |
| A(=t · Y/X) | — | 12.5 | 25 | 50 | 100 | 125 |
| Set aqueous solution temperature (° C.) | 50 | 50 | 50 | 50 | 50 | 50 |

TABLE 4-continued

| Treatment time t (min) | 0 | 15 | 30 | 60 | 120 | 150 |
|---|---|---|---|---|---|---|
| Measurement according to KI method (ppm) | 0 | 85.0 | 129.6 | 200.2 | 315.8 | 341.3 |
| Maximum dilution factor having a microbicidal effect | — | 500-fold | 500-fold | 500-fold | 1000-fold | 500-fold |

TABLE 5

| Microbe | Microbe | No. of microbes administered | Eradication time (min) | Maximum dilution factor having a microbicidal effect |
|---|---|---|---|---|
| Escherichia coli | Escherichia coli | $2.4 \times 10^6$ | 10 | 2000 -fold |
| Salmonella enterica | Salmonella enterica | $7.1 \times 10^6$ | 10 | 800 -fold |
| Staphylococcus aureus | Staphylococcus aureus | $8.7 \times 10^6$ | 10 | 200 -fold |
| Enterococcus faecalis | Enterocaccas faecalis | $3.1 \times 10^6$ | 10 | 400 -fold |
| Campylobacter jejuni | Campylobacter jejuni | $1.6 \times 10^7$ | 10 | 400 -fold |
| Bacillus subtilis (spore) | Bacillus subtilis (spore) | $1.1 \times 10^3$ | 60 | 10 -fold |
| Helicobacter cinaedi | Helicobacter cinaedi | $6.4 \times 10^6$ | 10 | 1000 -fold |
| Helicobacter pylori | Helicobacter pylori | $1.4 \times 10^6$ | 10 | 200 -fold |
| Vibrio cholerae (O1 Ogawa) | Vibrio cholerae (O1 Ogawa) | $1.1 \times 10^5$ | 60 | 800 -fold |
| Vibrio cholerae (O1 Inaba) | Vibrio cholerae (O1 Inaba) | $3.8 \times 10^4$ | 60 | 800 -fold |
| Vibrio cholerae (O139) | Vibrio cholerae (O139) | $1.3 \times 10^5$ | 60 | 800 -fold |
| Treponema spp. | Treponema spp | — | 10 | 100 -fold |
| Vibrio parahaemolyticus | Vibrio parahaemolyticus | $4.0 \times 10^5$ | 10 | 8000 -fold |
| Bacillus anthracis (single seedling strain) | Bacillus anthracis | $2.0 \times 10^5$ | 10 | 10 -fold |
| Bacillus anthracis (two seedling strain) | Bacillus anthracis | $5.0 \times 10^5$ | 10 | 10 -fold |
| Clostridium botulinum (botulinum toxin type A) | Clostridium botulinum | $1.0 \times 10^7$ | 60 | 1 -fold |
| Clostridium botulinum (botulinum toxin type A)(spore) | Clostridium botulinum (spore) | $1.5 \times 10^6$ | 60 | 10 -fold |
| Clostridium botulinum (botulinum toxin type B) | Clostridium botulinum | $1.6 \times 10^5$ | 60 | 10 -fold |
| Clostridium botulinum (botulinum toxin type B)(spore) | Clostridium botulinum (spore) | $2.3 \times 10^5$ | 60 | 10 -fold |

BRIEF DESCRIPTION OF THE REFERENCE SYMBOLS

1 Microbicide manufacturing device
3 Reservoir (water storage tank)
5 Microbubble generation unit
13 Motor
15 Pump
17 Suction port
21 Gas suction path
23 Ozone supply means
27 Connecting path
29 Ozone dissolving unit
31 Sealed vessel
33 Inlet pipe
41 Outlet pipe
43 Outlet port
43F Flange member
47 Connecting path (connecting pipe)
49 Bubble generation nozzle
51 Nozzle body
53 Communicating hole
55 Bubble generation cartridge
57 Cartridge body
59 Screen member
61 Orifice
63 Fixture
65 Pressure release chamber
67 Through hole
69 Stirring chamber

The invention claimed is:

1. A method for manufacturing a microbicide, comprising:
a step for preparing an inorganic aqueous solution containing an inorganic component having seawater as a raw material thereof,
an ozone mixing step for mixing ozone into the inorganic aqueous solution, and
a stirring step for stirring the inorganic aqueous solution mixed with ozone and passing through a bubble generation nozzle; wherein,
when the amount of inorganic aqueous solution treated in the ozone mixing step and the stirring step is defined as X liters and the treatment rate of the ozone mixing step and the stirring step is defined as Y liters/minute, then the microbicide is manufactured by alternately repeating the ozone mixing step and the stirring step for A·X/Y minutes, where A is a value from 40 to 80, and
the inorganic aqueous solution contains three-fold diluted bittern-containing water with water and the bittern-containing water contains 12% to 30% by weight $MgCl_2$ as Mg ions, 10 mg/liter to 100 mg/liter of Ca ions, 100 mg/liter to 1000 mg/liter of K ions and 100 mg/liter to 1000 mg/liter of Na ions, and
the temperature of the inorganic aqueous solution in the ozone mixing step and the stirring step is 0° C. to 10° C.

2. The method for manufacturing a microbicide according to claim 1, wherein the temperature of the inorganic aqueous solution in the ozone mixing step and the stirring step is 4° C. to 10° C.

3. The method for manufacturing a microbicide according to claim 1, wherein the inorganic component contained in the inorganic aqueous solution further contains at least one ion selected from the group consisting of sulfur, boron, lithium, silicon, zinc, iron and strontium ions.

4. The method for manufacturing a microbicide according to claim 1, wherein the inorganic aqueous solution does not contain organic matter.

5. The method for manufacturing a microbicide according to claim 1, wherein the bubble generation nozzle is a bubble generation nozzle for generating microbubbles.

6. The method for manufacturing a microbicide according to claim 1, wherein the A is 45 to 60.

7. The method for manufacturing a microbicide according to claim 1, wherein the A is 45 to 60, and the temperature of the inorganic aqueous solution in the ozone mixing step and the stirring step is 4° C. to 10° C.

8. The method for manufacturing a microbicide according to claim 1, wherein the A is 45 to 60, and the temperature of the inorganic aqueous solution in the ozone mixing step and the stirring step is 4° C.

9. The method for manufacturing a microbicide according to claim 1, wherein, in the stirring step, the inorganic aqueous solution mixed with the ozone is stirred in a sealed vessel, a location of an inlet port of the inorganic aqueous solution mixed with the ozone is above the level of liquid in the sealed vessel.

10. The method for manufacturing a microbicide according to claim 1, wherein the microbicide is a microbicide for eradicating at least one of viruses, bacteria, fungi and spores.

11. The method for manufacturing a microbicide according to claim 2, wherein the microbicide is a microbicide for eradicating at least one of viruses, bacteria, fungi and spores.

12. The method for manufacturing a microbicide according to claim 3, wherein the microbicide is a microbicide for eradicating at least one of viruses, bacteria, fungi and spores.

13. The method for manufacturing a microbicide according to claim 4, wherein the microbicide is a microbicide for eradicating at least one of viruses, bacteria, fungi and spores.

14. The method for manufacturing a microbicide according to claim 5, wherein the microbicide is a microbicide for eradicating at least one of viruses, bacteria, fungi and spores.

15. The method for manufacturing a microbicide according to claim 6, wherein the microbicide is a microbicide for eradicating at least one of viruses, bacteria, fungi and spores.

16. The method for manufacturing a microbicide according to claim 10, wherein the microbicide is a microbicide for eradicating a virus in the form of low pathogenic avian influenza virus of H3N3 type.

17. The method for manufacturing a microbicide according to claim 10, wherein the microbicide is a microbicide for eradicating at least one type of bacteria selected from *Escherichia coli, Salmonella enterica, Staphylococcus aureus, Enterococcus faecalis, Campylobacter jejuni, Helicobacter cinaedi, Helicobacter pylori, Vibrio cholerae, Vibrio parahaemolyticus, Bacillus anthracis* of single seedling strain, or two seedling strain, *Treponema* species and *Clostridium botulinum*.

18. The method for manufacturing a microbicide according to claim 10, wherein the microbicide is a microbicide for eradicating a fungus in the form of *Aspergillus flavus* or a yeast-like fungus in the form of *Candida albicans*.

19. The method for manufacturing a microbicide according to claim 10, wherein the microbicide is a microbicide for eradicating spores of *Bacillus subtilis*.

\* \* \* \* \*